US012005248B2

(12) United States Patent
Vogt et al.

(10) Patent No.: US 12,005,248 B2
(45) Date of Patent: Jun. 11, 2024

(54) ROTOR BEARING SYSTEM

(71) Applicant: KARDION GMBH, Stuttgart (DE)

(72) Inventors: Andreas Vogt, Renningen (DE); Ingo Stotz, Ditzingen (DE); Johannes Bette, Leonberg (DE); Armin Schuelke, Aidlingen (DE); Xiang Li, Stuttgart (DE); Uwe Vollmer, Sindelfingen (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 795 days.

(21) Appl. No.: 17/054,884

(22) PCT Filed: May 16, 2019

(86) PCT No.: PCT/EP2019/062746
§ 371 (c)(1),
(2) Date: Jul. 13, 2021

(87) PCT Pub. No.: WO2019/219883
PCT Pub. Date: Nov. 21, 2019

(65) Prior Publication Data
US 2021/0346680 A1    Nov. 11, 2021

(30) Foreign Application Priority Data

May 16, 2018    (DE) ...................... 10 2018 207 611.1

(51) Int. Cl.
*A61M 60/82*    (2021.01)
*A61M 60/178*    (2021.01)
(Continued)

(52) U.S. Cl.
CPC .......... *A61M 60/82* (2021.01); *A61M 60/178* (2021.01); *A61M 60/216* (2021.01);
(Continued)

(58) Field of Classification Search
CPC .. A61M 60/82; A61M 60/178; A61M 60/216; A61M 60/419; A61M 60/824;
(Continued)

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| AU | 7993698 | 2/1999 |
| AU | 2002308409 | 12/2005 |

(Continued)

OTHER PUBLICATIONS

International Search Report for International Application No. PCT/EP2019/062746 dated Aug. 16, 2019.
(Continued)

*Primary Examiner* — Mark W. Bockelman
(74) *Attorney, Agent, or Firm* — Knobbe Martens Olson and Bear, LLP

(57) ABSTRACT

The invention relates to a rotor bearing system (1). Said system comprises a housing (80) in which a first permanent magnet (30) is mounted such that it can rotate about a first axis (105). A rotor (70) for conveying a liquid comprises a second hollow-cylindrical permanent magnet (40), which is mounted such that it can rotate about a second axis. The first permanent magnet (30) and the second permanent magnet (40) overlap axially at least partially, wherein the first permanent magnet (30) is disposed offset relative to the second permanent magnet (40). In the axial overlap region (160) of the first permanent magnet (30) and the second permanent magnet (40), the housing (80) is positioned between the two permanent magnets (30, 40). A first bearing (20) is configured for the relative axial positioning of the
(Continued)

rotor (70) and the housing (80) with respect to one another and for receiving an axial force resulting from the arrangement of the first permanent magnet (30) and the second permanent magnet (40), and a second bearing (10) and a third bearing (90) are configured for receiving radial forces and for positioning the axis of rotation of the second permanent magnet (40).

20 Claims, 4 Drawing Sheets

(51) Int. Cl.
    *A61M 60/216*     (2021.01)
    *A61M 60/419*     (2021.01)
    *A61M 60/824*     (2021.01)
    *A61M 60/825*     (2021.01)
    *F04D 3/00*     (2006.01)
    *F04D 29/048*     (2006.01)
    *F04D 29/18*     (2006.01)
    *F16C 17/10*     (2006.01)
    *H02K 7/08*     (2006.01)
    *H02K 16/00*     (2006.01)

(52) U.S. Cl.
    CPC ........ *A61M 60/419* (2021.01); *A61M 60/824* (2021.01); *A61M 60/825* (2021.01); *F04D 3/00* (2013.01); *F04D 29/048* (2013.01); *F04D 29/181* (2013.01); *F16C 17/10* (2013.01); *H02K 7/088* (2013.01); *H02K 16/005* (2013.01); *F16C 2316/18* (2013.01)

(58) Field of Classification Search
    CPC ....... A61M 60/825; A61M 60/13; F04D 3/00; F04D 29/048; F04D 29/181; F04D 13/0606; F04D 29/0467; F16C 17/10; F16C 2316/18; F16C 17/26; H02K 7/088; H02K 16/005

See application file for complete search history.

(56) References Cited

U.S. PATENT DOCUMENTS

| | | | |
|---|---|---|---|
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,589,031 B2 | 7/2003 | Maeda et al. |
| 6,592,620 B1 | 7/2003 | Lancisi et al. |
| 6,595,743 B1 | 7/2003 | Kazatchkov et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |

(56) References Cited

U.S. PATENT DOCUMENTS

| | | |
|---|---|---|
| 7,014,620 B2 | 3/2006 | Kim |
| 7,022,100 B1 | 4/2006 | Aboul-Hosn et al. |
| 7,027,875 B2 | 4/2006 | Siess et al. |
| 7,011,620 B1 | 5/2006 | Siess |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |

(56) References Cited

U.S. PATENT DOCUMENTS

| | | |
|---|---|---|
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,814,053 B2 | 10/2020 | Throckmorton et al. |
| 10,857,273 B2 | 12/2020 | Hodges et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |

(56) References Cited

U.S. PATENT DOCUMENTS

| | | |
|---|---|---|
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,746,906 B1 | 9/2023 | Balta et al. |
| 11,754,075 B2 | 9/2023 | Schuelke et al. |
| 11,754,077 B1 | 9/2023 | Mohl |
| 11,759,622 B2 | 9/2023 | Siess et al. |
| 11,781,550 B2 | 10/2023 | Siess et al. |
| 11,804,767 B2 | 10/2023 | Vogt et al. |
| 11,806,116 B2 | 11/2023 | Tuval et al. |
| 11,833,278 B2 | 12/2023 | Siess et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,944,805 B2 | 4/2024 | Stotz |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0044266 A1 | 3/2004 | Siess et al. |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0138080 A1 | 5/2009 | Siess et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0298625 A1 | 11/2010 | Reichenbach et al. |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |

(56) References Cited

U.S. PATENT DOCUMENTS

| | | |
|---|---|---|
| 2016/0223086 A1 | 8/2016 | Balsells et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groβ-Hardt et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |

(56) References Cited

U.S. PATENT DOCUMENTS

| | | |
|---|---|---|
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2023/0001178 A1 | 1/2023 | Corbett et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |
| 2024/0102475 A1 | 3/2024 | Schuelke et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 19910872 A1 | 10/1999 |
| DE | 199 56 380 | 11/1999 |
| DE | 100 59 714 | 5/2002 |
| DE | 101 55 011 | 11/2005 |
| DE | 601 19 592 | 9/2006 |
| DE | 60119592 T2 | 9/2006 |
| DE | 20 2005 020 288 | 6/2007 |
| DE | 10 2008 060 357 | 6/2010 |
| DE | 10 2009 039 658 | 3/2011 |
| DE | 20 2009 018 416 | 8/2011 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 3 127 562 | 2/2017 |
| EP | 2 585 129 | 3/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |

(56) References Cited

FOREIGN PATENT DOCUMENTS

| | | |
|---|---|---|
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 2 344 218 | 4/2021 |
| EP | 3 436 104 | 4/2021 |
| EP | 3 749 383 | 4/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 3 795 208 | 10/2023 |
| EP | 4 149 606 | 10/2023 |
| EP | 3 157 596 | 11/2023 |
| EP | 4 061 470 | 11/2023 |
| FR | 1458525 | 3/1966 |
| GB | 0 648 739 | 1/1951 |
| GB | 2 213 541 | 8/1989 |
| GB | 2335242 A | 9/1999 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515375 | 9/2001 |
| JP | 2003-019197 | 1/2003 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 6572056 | 9/2019 |
| JP | 2020-072985 | 5/2020 |

(56) References Cited

FOREIGN PATENT DOCUMENTS

| | | |
|---|---|---|
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/088939 | 3/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

International Preliminary Report on Patentability and Written Opinion received in PCT Application No. PCT/EP2019/062746, dated Nov. 26, 2020 in 8 pages.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.

ROTOR BEARING SYSTEM

BACKGROUND

Field

The present invention relates to a rotor bearing system.

Description of the Related Art

A combination of a solid-body bearing and a passive magnetic axial coupling is known in the state of the art. A radial passive magnetic coupling for torque transmission, which has an axial offset of a coupling part, i.e. a preload, for adjusting the axial force, is known as well.

The use of an axial passive magnetic coupling leads to a high axial force on the bearing arrangement, and consequently to increased friction and increased wear. The axial force to be received by the bearing cannot be minimized, because said force is a direct function of the torque to be transmitted.

Further known is also an arrangement having two fixed bearings for axial and radial support of the rotor in pumps, in particular in pumps for cardiovascular support (VAD). In the case of preloaded bearings, the use of two solid-body bearings represents an overdetermined bearing arrangement in which the preload is reduced by wear of the loaded bearing or bearings until there is a small amount of play and the bearing arrangement becomes underdetermined, which is disadvantageous. A thermally induced elongation or expansion of the rotor can furthermore not be compensated, so that the rotor may jam between the two axial bearings.

SUMMARY

The object of the invention is to provide a rotor bearing system in which less friction and therefore less wear occurs.

This object is achieved by the rotor bearing system specified in Claim 1. Advantageous embodiments of the invention are specified in the dependent claims.

A rotor bearing system according to the invention is in particular used for the contactless transmission of a torque to a rotating rotor in combination with the support thereof in axial and radial direction.

A rotor bearing system according to the invention comprises a housing, in which a first in particular cylindrical permanent magnet is mounted such that it can rotate about a first axis. A rotor bearing system according to the invention further comprises a rotor comprising a second hollow-cylindrical permanent magnet, which is mounted such that it can rotate about a second axis. The rotor preferably comprises a hollow-cylindrical part in which the second hollow-cylindrical permanent magnet is disposed.

In a rotor bearing system according to the invention, the first permanent magnet and the second permanent magnet overlap axially at least partially, wherein the first permanent magnet is disposed offset, in particular axially, relative to the second permanent magnet.

The phrase "the first permanent magnet is disposed axially offset relative to the second permanent magnet" means that an axial center of the first permanent magnet is disposed axially offset relative to an axial center of the second permanent magnet.

The axial center of a permanent magnet is hereby calculated as the point between the one axial end of the permanent magnet and the opposite other axial end of the permanent magnet. One axial end is located on an axial longitudinal axis of the permanent magnet.

The housing between the two permanent magnets is furthermore located in the axial overlap region of the first permanent magnet and the second permanent magnet.

The rotor bearing system also comprises a first bearing for the relative axial positioning of the rotor and the housing with respect to one another and for receiving an axial force resulting from the arrangement of the first permanent magnet and the second permanent magnet.

The rotor bearing system further comprises a second bearing and a third bearing for receiving radial forces and for positioning the axis of rotation of the second permanent magnet.

The axial offset of the first and the second permanent magnet relative to one another produces a force in axial direction between these bodies which, depending on the type of magnetization, acts in or preferably counter to the offset direction. This in particular makes it possible to set a positive, negative or disappearing axial force resulting from the coupling and other operating forces, e.g. from flow forces, in a defined manner, without simultaneously significantly reducing the transmittable torque. For this purpose, the axial force exerted on the rotor from the flow can be determined first, e.g. by evaluating flow simulations. The relationship between axial offset and magnetic axial force can be determined from magnetic simulations and/or measurements. An offset can then be selected for the design, in which the magnetic axial force at least compensates the flow axial force, preferably overcompensates the flow axial force by a safety factor.

In combination with the first bearing, i.e. an axial bearing, a defined axial force required for the bearing function can thus be set via the relative axial offset. Said axial force can be selected such that the first bearing can be operated within the allowable range with regard to friction and wear. It is preferred that the axial bearing is operated in constant contact, i.e. the magnetic axial force must at least compensate the flow axial force at all times.

In contrast to a solution realized in the state of the art with two axial solid-body bearings having the above-described disadvantages, the solution described here comprises only one axial solid-body bearing and thus avoids overdetermination or underdetermination. The specifically adjustable axial force from the magnetic coupling also ensures that the axial support by the solid-body bearing is sufficient in only one direction.

According to a preferred embodiment, the first permanent magnet and the second permanent magnet are arranged coaxially. This advantageously enables efficient coupling of the first and second permanent magnet.

It is further preferred that an axis of rotation of the rotor and an axis of the second permanent magnet are coaxial. This advantageously ensures that the rotor and the second permanent magnet are disposed in a symmetrical manner, which also facilitates the production of the rotor.

It is further preferred that an axis of rotation of the shaft and an axis of the first permanent magnet are coaxial. This advantageously ensures that the shaft and the first permanent magnet are easy to produce.

It is further preferred that an axis of rotation of the shaft and an axis of rotation of the rotor are coaxial. This advantageously ensures that the coupling between the first and the permanent magnet is efficient.

According to a preferred embodiment, the rotor comprises a conical or tapered part, which adjoins the hollow-cylindrical part. It is preferred here that the axis of the cone and the axis of rotation of the rotor, which is preferably coaxial with the axis of the second permanent magnet, are coaxial. The base of the conical part adjoins the hollow-cylindrical part in the direction of the bearing mounted between the rotor and the housing. The outer circumference of the base of the cone is hereby connected to the annular opening at an axial end of the hollow-cylindrical part.

According to another preferred embodiment, the second bearing is mounted on the end of the rotor facing away from the housing, i.e. on the end of the conical part facing away from the housing. It is preferred that the bearing is mounted between the rotor and an affixed component, whereby the affixed component is preferably permanently connected to the housing.

According to another preferred embodiment, the rotor comprises blades on the outer periphery of the rotor, preferably on the conical part of the rotor, which, when the rotor rotates, transports a liquid from the end of the rotor facing away from the housing toward the housing. It is preferred that the rotor comprises holes, so that the liquid is drawn from outside the rotor into a gap formed by the inner side of the hollow-cylindrical part of the rotor and an outer side of the housing, to then flow from the inside of the hollow-cylindrical part of the rotor flow through the conical part of the rotor to the end of the rotor facing away from the housing.

According to a preferred embodiment, the first bearing and the third bearing together form a combined axial and radial bearing which serves to receive axial and radial forces. The combined axial and radial bearing preferably comprises an axial bearing and a radial bearing.

According to a preferred embodiment, the first bearing and the third bearing are disposed between the housing and the rotor and the second bearing is disposed on the rotor. The first and third bearing are preferably a combined axial and radial bearing. The axial offset of the first and second permanent magnet is hereby set such that the housing is pressed in the direction of the rotor and/or the rotor is pressed in the direction of the housing.

According to a preferred embodiment, the combined axial and radial bearing is a solid-body bearing, which, in the rotor, preferably comprises a ball which rotates in a cone provided on the housing, thus allowing both radial and axial forces to be received. The material of the ball and/or the cone preferably comprises or consists of monocrystalline corundum or sapphire. These materials are ideal because of their high wear resistance.

According to a preferred embodiment, the first bearing and the third bearing are disposed on the rotor and the second bearing is disposed between the housing and the rotor.

The first and third bearing are preferably mounted on an end of the rotor facing away from the housing. The first and third bearing are mounted between the end of the rotor facing away from the housing and an affixed component, whereby the affixed component is preferably permanently connected to the housing.

The first and third bearing preferably form a combined axial and radial bearing. According to a preferred embodiment, the combined axial and radial bearing is a solid-body bearing, which preferably comprises a ball disposed in the rotor, which rotates in a cone attached to the affixed component, by means of which both radial and axial forces can be received. The material of the ball and/or the cone preferably comprises or consists of monocrystalline corundum or sapphire.

According to a preferred embodiment, the first and the third bearing are realized by two different structural elements. For example, the axial bearing function can be realized by the contact of a ball or other preferably convex surface disposed in the rotor with a preferably flat plate mounted on the housing. The radial bearing function can, for example, be realized by a hydrodynamic sliding bearing on the periphery of the rotor, preferably on the hollow-cylindrical part of the rotor at the level of the second permanent magnet.

The second or third bearing is preferably a hydrodynamic sliding bearing. The second or third bearing is preferably disposed on the periphery of the rotor.

According to a preferred embodiment, the housing is a motor housing which, in its interior, comprises a rotatably mounted shaft and the first permanent magnet disposed on said shaft. It is further preferred that a motor which drives the shaft is disposed in the motor housing. It is further preferred that the motor is completely sealed off from the environment by the motor housing, so that liquid cannot enter the motor housing and the motor, and substances from the interior of the motor also cannot leak into the surrounding liquid.

According to a preferred embodiment, both the first permanent magnet and the second permanent magnet respectively comprise at least one pole pair. The first permanent magnet preferably comprises the same number of pole pairs as the second permanent magnet. It is further preferred that the number of pole pairs is greater than two. This can advantageously ensure that the transmittable torque can be increased.

According to a preferred embodiment, the axial force originating from the coupling, i.e. a magnetic force, which results from the offset of the first and second permanent magnet and acts on the rotor, is selected to be greater than the hydraulic force. In this case, the hydraulic force is a reaction force which acts on the rotor and counteracts the direction of flow. This feature advantageously ensures that, at the first bearing, the rotor is pressed in the direction of the housing, so that the rotor and the housing do not lose contact at the first bearing. The magnetic axial force preferably overcompensates the flow axial force by a safety factor.

According to another preferred embodiment, the axial force originating from the coupling is selected to be smaller than the hydraulic force. The first bearing is only in contact when the system is at a standstill. This means that the hydraulic force on the rotor is at the nominal operating point. In this case, the axial position during operation is entirely determined by the balance between the magnetic force and the hydraulic force.

According to a preferred embodiment, both the first permanent magnet and the second permanent magnet respectively comprise at least two axial segments.

By partitioning the radial coupling, which is realized by the first and second permanent magnet, into two or more segments in axial direction with a simultaneous axial offset of the segments relative to one another, the axial force can advantageously be increased. With comparable dimensions, overall length and outer diameter, the transmittable torque decreases, which can, however, be compensated by an axial elongation of the radial coupling or an increase in the number of pole pairs. Thus, both the torque and the axial force can be adjusted via the number of pole pairs, the exterior dimensions and the partitioning with distances between the segments. The number of segments and the distance between the segments determines the amount of axial force.

This measure can be taken, for example, if the magnetic axial force is insufficient to reliably compensate the flow force.

The number of segments of the first permanent magnet is preferably exactly the same as the number of segments of the second permanent magnet. This simplifies production and increases the symmetry of the device.

The first permanent magnet preferably has the same overall axial length as the second permanent magnet. The overall axial length is the sum of all segments and all spacers. It is hereby assumed that there is no gap between a segment and a spacer or another segment.

According to a preferred embodiment, one spacer is respectively disposed between adjacent segments of the first permanent magnet and/or the second permanent magnet. This can advantageously ensure that the two adjacent segments of a permanent magnet are spaced apart from one another by a predetermined axial distance. This also makes it possible to realize an axial preload, for example in order to be able to produce a defined axial force for a bearing function.

According to a preferred embodiment, at least one spacer comprises or consists of plastic, aluminum, titanium or another non-magnetic material. This has the advantage that the material of the spacer has little or no influence on the magnetic field, since said material is non-ferromagnetic.

According to a preferred embodiment, the second permanent magnet comprises a device for magnetic return. This device is preferably disposed on the outer side of the second permanent magnet. In addition to advantages in terms of production technology, this has the advantage that the torque of the coupling is increased, because fewer stray fields are lost.

According to a preferred embodiment, the first permanent magnet and/or the second permanent magnet has a radial, parallel or diametrical magnetization. These are common types of magnetization, which the person skilled in the art can adapt to the given circumstances of each individual case.

According to a preferred embodiment, the first permanent magnet and/or the second permanent magnet comprises a permanent magnet which comprises or is a Halbach array, i.e. which in particular has the magnet configuration of a Halbach array.

In the present case, a permanent magnet having the magnet configuration of a Halbach array is a permanent magnet in which the magnetic flux density is low on one side, the so-called weak side, because the magnetic flux is essentially canceled there, and high on another side, the so-called strong side, because the magnetic flux is amplified there.

In the present case, a Halbach array is an arrangement of magnets as they are described at the link https://en.wikipedia.org/wiki/Halbach_array, to which reference is hereby made and the disclosure of which is fully incorporated into the description of this invention.

The magnet configuration of a Halbach array can be formed by permanent-magnetic segments which are assembled and the magnetization direction of which relative to one another is tilted 90° with respect to a preferred direction, e.g. with respect to the direction of a longitudinal axis of the arrangement. It is thus possible to achieve a side-dependent flux amplification. For further information, please also refer to the relevant technical literature concerning Halbach arrays.

The first permanent magnet and/or the second permanent magnet is or are preferably a permanent magnet which comprises or is a Halbach array. This feature advantageously ensures that the magnetic flux can be concentrated on one side of the Halbach array (strong side). This is particularly advantageous in the case of the second permanent magnet, which is disposed on the outside, whereby the strong side of the Halbach array of the second breakdown magnet [sic] is directed toward the first permanent magnet.

The first permanent magnet and the second permanent magnet are magnetized such that a rotation of the first permanent magnet sets the second permanent magnet in rotation and vice versa. This characteristic is necessary to be able to transmit torque from the one permanent magnet to the other permanent magnet without contact.

Preferably, the first permanent magnet and the second permanent magnet together form a magnetic coupling which, due to the preferably radially directed magnetic field lines, is preferably a radial magnetic coupling.

According to a preferred embodiment, an axial force of the rotor bearing system can be freely adjusted by varying at least one of the following list. The list includes: a pole pair number of the first permanent magnet and the second permanent magnet; the dimensions of the segments of the first permanent magnet; the dimensions of the segments of the second permanent magnet; distances between adjacent segments of the first permanent magnet and the second permanent magnet; distances between adjacent segments of the magnetic return; axial lengths of spacers between segments of the first permanent magnet and the second permanent magnet and segments of the magnetic return; a magnetization of the first permanent magnet; a magnetization of the second permanent magnet; a flow force which acts on the rotor during proper use; and an offset of the first permanent magnet relative to the second permanent magnet.

The person skilled in the art knows that the variables mentioned in the list influence the axial force. By varying at least one of the values in the list, preferably several values in the list, the axial force can be freely adjusted within predetermined limits. This can advantageously ensure that the axial force can appropriately be adapted to the given circumstances of each individual case.

The rotor preferably comprises at least one bore or at least one hole, preferably bores or holes. This advantageously ensures that the liquid transported by the rotor can flow into a space or gap between the rotor and the housing. This enables heat, produced for example by friction or by eddy currents in a possibly metal housing, to be dissipated. Furthermore, the continuous flow of the medium ideally prevents deposits of solid particles of the medium in the region of the gap and the bearing.

BRIEF DESCRIPTION OF THE DRAWINGS

Advantageous design examples of the invention are shown in the drawings and are explained in more detail in the following description.

DETAILED DESCRIPTION

Figure 1:
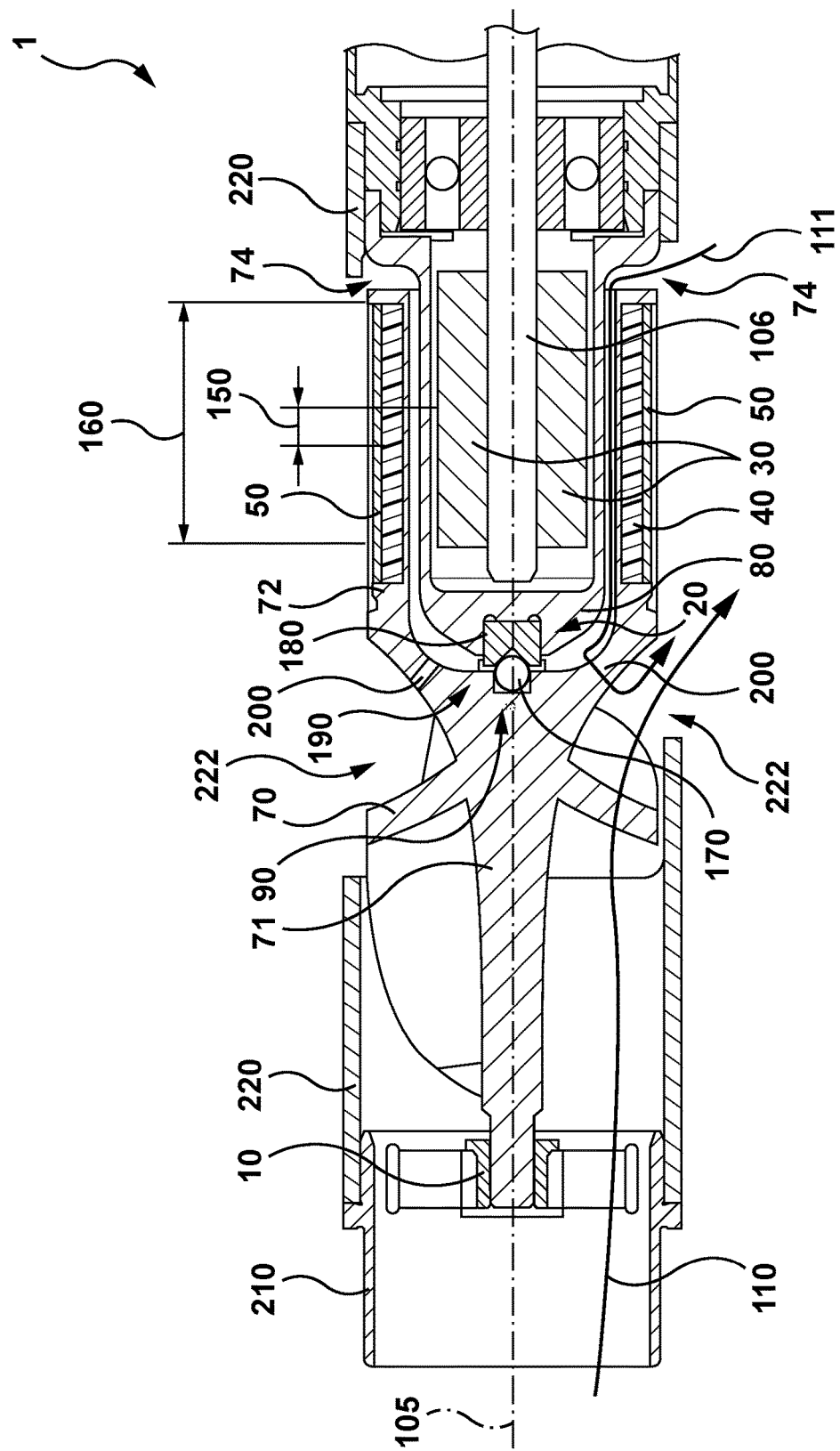
FIG. 1 shows a rotor bearing system according to an embodiment of the invention.

FIG. 1 shows a rotor bearing system 1 with contactless torque transmission and a radial and axial bearing of a rotor, which is designed in the form of a pump for cardiovascular support (VAD), for example.

The rotor bearing system 1 comprises a housing 80, here a motor housing, in which a first cylindrical permanent magnet 30 is seated and mounted on a shaft 106 driven by a not depicted motor such that it can rotate about a first axis 105. The housing 80 has an outer diameter of 3.5 mm.

The rotor bearing system 1 further comprises a rotor 70 for conveying a liquid, wherein the rotor 70 comprises a second hollow-cylindrical permanent magnet 40, which is likewise mounted such that it can rotate about the first axis 105. The second hollow-cylindrical permanent magnet 40 is mounted in a hollow-cylindrical part 72 of the rotor 70.

The second hollow-cylindrical permanent magnet 40 comprises a magnetic return 50 on its outer side.

The first permanent magnet 30 has an outer diameter of 3 mm, a magnet height of 1 mm and a length of 5 mm. The second permanent magnet 40 has an outer diameter of 5 mm, a magnet height of 0.5 mm and a length of 5 mm. The rotor 70 has an outer diameter of 5.3 mm and a length of 15 mm.

The rotor 70 is designed as an impeller, which converts the mechanical power transmitted by the coupling into hydraulic power for supporting a blood flow against a blood pressure.

The rotor 70 further comprises a conical or tapered part 71, which adjoins the hollow-cylindrical part 72. The outer circumference of the base of the conical part 71 is connected to the annular opening at an axial end of the hollow-cylindrical part 72.

The first permanent magnet 30 and the second permanent magnet 40 overlap axially at least partially in the axial region identified with the reference sign 160.

The first permanent magnet 30 is hereby disposed axially offset relative to the second permanent magnet 40. The centers of the first permanent magnet 30 and the second permanent magnet 40 are marked by vertical lines and the axial offset 150 is drawn in between these two dashed lines.

As a result of the axial offset 150, the second permanent magnet 40 experiences a force which, in FIG. 1, is directed toward the right, so that a ball 170 disposed in the rotor 70 is pressed onto a cone 180 mounted in the housing 80, so that a first bearing 20 and a third bearing 90, which here form a combined axial and radial bearing 190, is kept in contact. During proper use, the ball 170 rotates in the cone 180, as a result of which both radial and axial forces can be received. The combined axial and radial bearing 190 here is a solid-body bearing. The ball 170 is disposed in the conical part 71. The axial and radial bearing function is achieved by combining the two elements ball 170 and cone 180.

The ball 170 has a diameter of 0.5 mm. The cone 180 has a diameter of 1 mm, a height of 0.8 mm and a cone angle of 90°.

The axial bearing function of the combined bearing 190 functions as the first bearing and is used for the relative axial positioning of the rotor 70 and the housing 80 or the shaft 106 relative to one another, and also for receiving an axial force resulting from the arrangement of the first permanent magnet 30 and the second permanent magnet 40.

The axial force in the rotor bearing system 1 can furthermore be freely adjusted, as a result of which the acting forces can be optimally adjusted.

In the overlap region 160 and in the region between the overlap region 160 and the rotor 70, the housing 80, which comprises the first permanent magnet 30, is surrounded by the rotor 70, in particular by the interior of the hollow-cylindrical part 72 of the rotor 70. A hollow-cylindrical channel 74 through which the liquid can flow is thus formed between the housing 80 and the rotor 70. In order to allow liquid to flow continuously from outside the conical part 71 of the rotor 70 into the channel 74, bores 200 are drilled into the rotor 70, preferably in the conical part 71 of the rotor 70, or at a transition from the conical part 71 to the hollow-cylindrical part 72 of the rotor 70. The flow direction of the liquid is indicated by arrow 110. Arrow 111 indicates a direction of flow of liquid through the channel 74.

A second bearing 10, which is designed as a radial, hydrodynamic and blood-lubricated sliding bearing, is mounted on the end of the conical part 71 of the rotor 70 facing away from the housing 80. The second bearing 10 is used to receive radial forces and to position the axis of rotation of the second permanent magnet 40, which is disposed in the rotor 70. The second bearing 10 is disposed between the rotor 70 and an insert 210 which is mounted, in particular clamped or press-fitted, on a second housing 220 in an annular end, which is in turn mounted on the housing 80. The second housing 220 forms an outer skin of the rotor bearing system 1, whereby numerous outlet windows 222 are present in the second housing 220, which can also be referred to as an impeller housing. The insert 210 is preferably a spider bearing that can be glued, welded or press-fitted into the second housing 220. The spider bearing 210 has an outer diameter of 6 mm and a length of 3 mm. The second housing 220 has an outer diameter of 6 mm, a length of 18 mm and a wall thickness of 0.25 mm.

The bearing 10 has a diameter of 1 mm and a length of 1 mm.

As a result of the axial offset 150 between the first permanent magnet 30 and the second permanent magnet 40 established by the design, in the design example of FIG. 1 a defined axial force acts on the rotor 70 in the direction of the motor; i.e. from left to right in the design example of FIG. 1. This force is counteracted by a hydraulic force on the rotor 70, i.e. from right to left in the design example of FIG. 1. In the present case, the axial force originating from the coupling of the first permanent magnet 30 and the second permanent magnet 40 is selected to be slightly greater than the hydraulic force. On the one hand, this ensures that the rotor 70 is always in a defined axial position and, on the other hand, that the combined axial and radial bearing 190 is not unnecessarily loaded. Consequently, friction and wear are kept low. To optimize the friction and wear behavior, the cone angle of the cone 180 can also be increased, whereby a sufficient radial load-bearing capacity has to be ensured.

Figure 2:
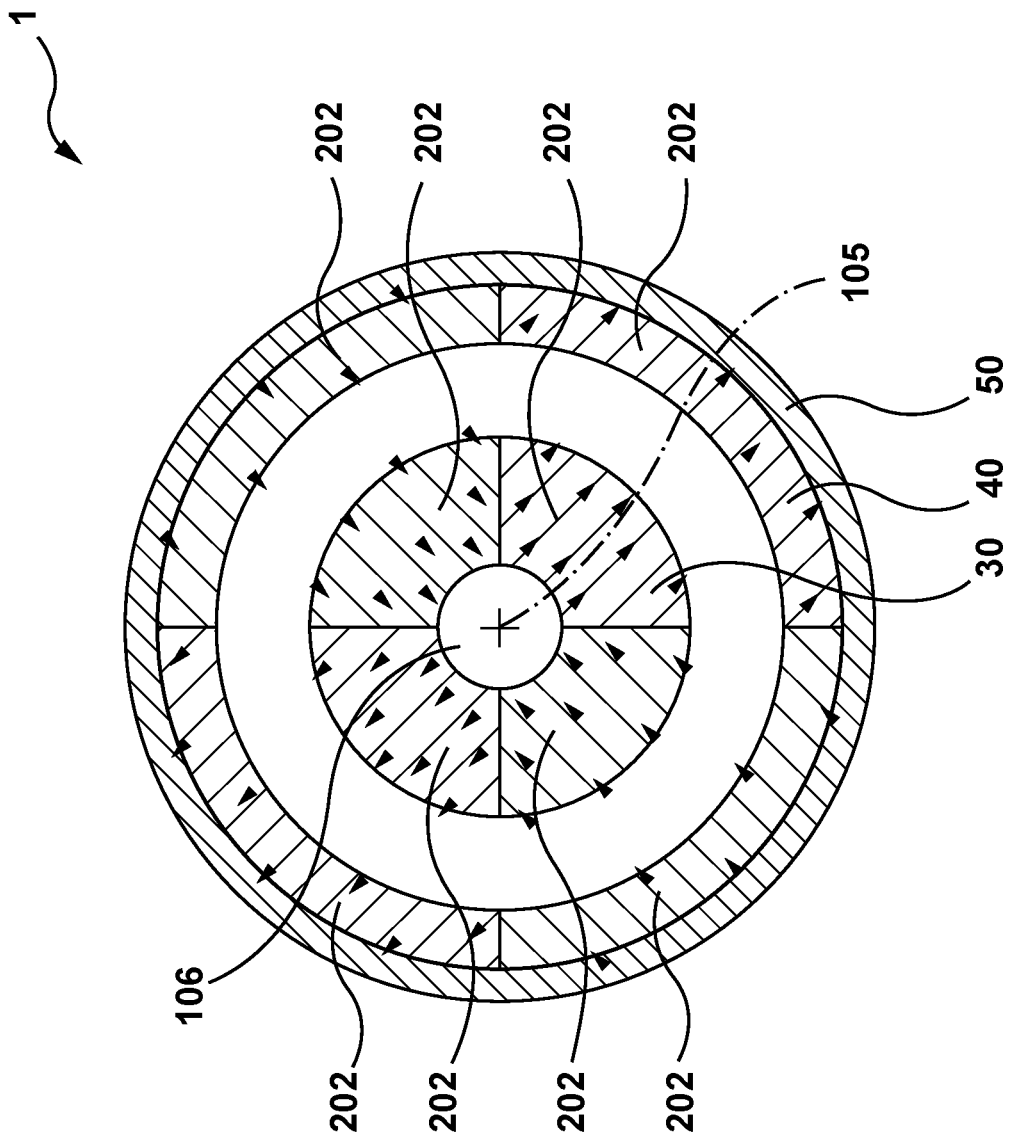
FIG. 2 shows a sectional view through an embodiment of the rotor bearing system according to the invention at a position in which the first permanent magnet, which is mounted in the housing, and the second permanent magnet, which is disposed in the rotor, overlap.

FIG. 2 shows a sectional view of the rotor bearing system 1 at a position in which the first permanent magnet 30, which is mounted in the housing 80, and the second permanent magnet 40, which is disposed in the hollow-cylindrical part 72 of the rotor 70, overlap axially. It can be seen that the first permanent magnet 30 is seated on the shaft 106 which is driven by the motor and is mounted such that it can rotate about the first axis 105. It can also be seen that the second permanent magnet 40 is likewise mounted such that it can rotate about the first axis 105. Both the first permanent magnet 30 and the second permanent magnet 40 comprise two pole pairs, i.e. four poles 202 each, which are respectively radially magnetized as indicated by small arrows.

Figure 3:
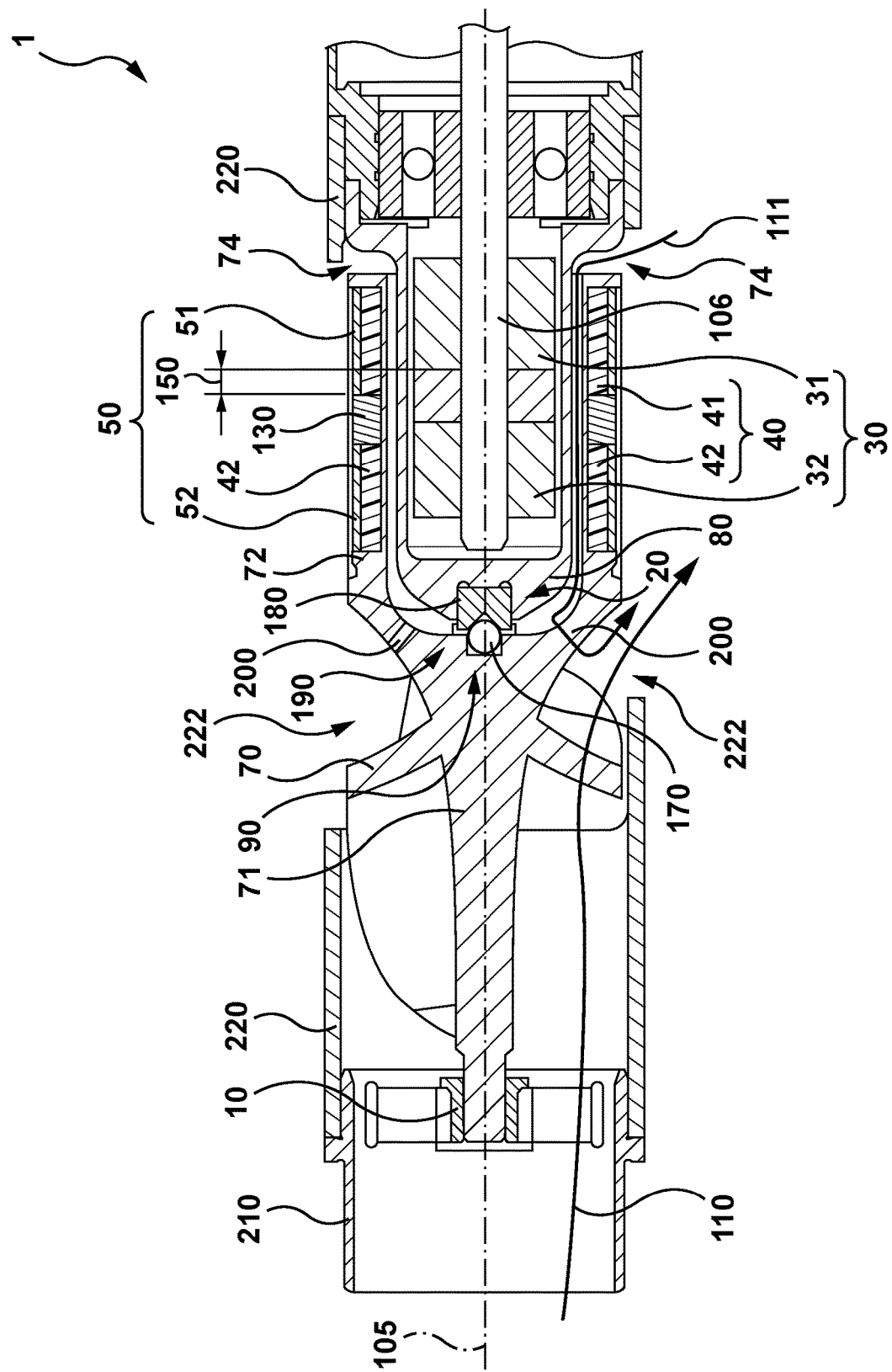
FIGS. 3 and 4 respectively show a rotor bearing system according to further embodiments of the invention.

FIG. 3 shows a rotor bearing system 1 in a similar embodiment as the rotor bearing system 1 of FIG. 1. The present embodiment differs from the embodiment of FIG. 1 in that the first permanent magnet 30, the second permanent magnet 40 and the magnetic return 50 are all divided into two axial segments.

The first permanent magnet 30 comprises the segments 31 and 32, the second permanent magnet 40 comprises the segments 41 and 42, and the magnetic return 50 comprises the segments 51 and 52. The segments 31, 41 and 51 are disposed on the motor side and the segments 32, 42 and 52 are disposed on the side facing the rotor 70.

A hollow-cylindrical and non-magnetic spacer 130, which is likewise mounted on the shaft 106, is disposed between the segments 31 and 32. A further hollow-cylindrical and non-magnetic spacer 130 is disposed between the segments 41 and 51 on the one side and the segments 42 and 52 on the other.

The segmentation in combination with the offset 150 between the two axial halves leads to an increase in the magnetic axial force while, at the same time, the transmittable torque decreases. This measure is taken in the present case because the magnetic axial force is insufficient to reliably compensate the flow force.

Figure 4:
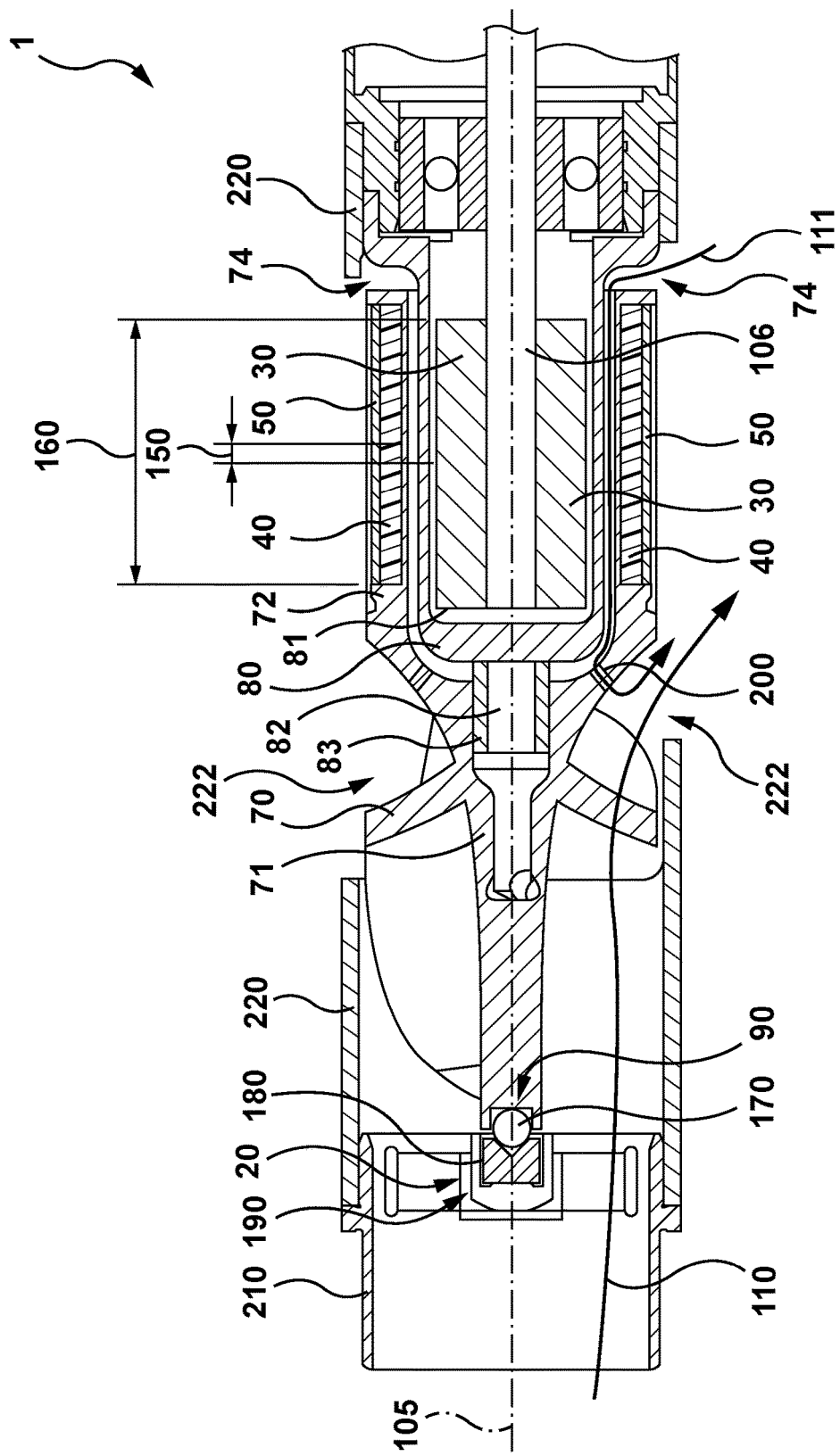

FIG. 4 shows a rotor bearing system 1 in a similar embodiment as the rotor bearing system 1 of FIGS. 1 and 3. The present embodiment differs from the embodiment of FIG. 1 in that, on the one hand, the position of the second bearing 10 is interchanged with the position of the first bearing 20 and the third bearing 90 and, on the other hand, the axial offset 150 between the first permanent magnet 30 and the second permanent magnet 40 points in the opposite direction as in the embodiment of FIG. 1. In the embodiment of FIG. 4, the axial offset 150 is 1 mm.

The first permanent magnet 30 and the second permanent magnet 40 overlap axially at least partially in the axial region identified with the reference sign 160. The first permanent magnet 30 is hereby disposed axially offset relative to the second permanent magnet 40. The centers of the first permanent magnet 30 and the second permanent magnet 40 are marked by vertical dashed lines and the axial offset 150 is drawn in between these two vertical dashed lines. In contrast to the embodiment of FIG. 1, viewed from the housing 80, the first permanent magnet 30 is axially offset relative to the second permanent magnet 40 in the direction of the rotor 70. Between the first permanent magnet 30 and the second permanent magnet 40 in the design example of FIG. 4, there is therefore a defined axial force which acts on the rotor 70 and is directed from the housing 80 toward the rotor 70 along the axis 105; i.e. from right to left in the design example of FIG. 4. A hydraulic force acts on the rotor 70 in the same direction, i.e. likewise from right to left in the design example of FIG. 4.

The advantage of this arrangement is that both the magnetic and the hydraulic axial force on the rotor 70 point in the same direction, namely upstream, as a result of which the rotor 70 is continuously pressed into the combined axial and radial bearing 190.

The first bearing 20 and the third bearing 90 here too form a combined axial and radial bearing 190, which is mounted on the end of the conical part 71 of the rotor 70 facing away from the housing 80. The combined bearing 190 is disposed between the rotor 70 and an insert 210 which is mounted, in particular clamped, on a second housing 220 in an annular end, which is in turn mounted on the housing 80. A ball 170, which is disposed on the end of the conical part 71 of the rotor 70 facing away from the housing, is hereby pressed onto a cone 180 mounted on the insert 210.

The second bearing 10, which is configured as radial, hydrodynamic sliding bearing, is used to receive radial forces and to position the axis of rotation of the second permanent magnet 40, which is disposed in the rotor 70. The second bearing 10 is disposed between the housing 80 and the rotor 70. In contrast to the embodiment of FIG. 1, behind a wall 81 facing toward the rotor 70, the housing 80 of the embodiment of FIG. 4 comprises a cylindrical journal 82 which continues as an extension of the shaft 106 in the direction of the rotor 70. The journal 82 is surrounded by a bearing shell 83 of the radial sliding bearing which forms the second bearing 10.

In summary, the following preferred features of the invention should in particular be noted:

The invention relates to a rotor bearing system 1. Said system comprises a housing 80 in which a first permanent magnet 30 is mounted such that it can rotate about a first axis 105. A rotor 70 for conveying a liquid comprises a second hollow-cylindrical permanent magnet 40, which is mounted such that it can rotate about a second axis. The first permanent magnet 30 and the second permanent magnet 40 overlap axially at least partially, wherein the first permanent magnet 30 is disposed offset relative to the second permanent magnet 40. In the axial overlap region 160 of the first permanent magnet 30 and the second permanent magnet 40, the housing 80 is positioned between the two permanent magnets 30, 40. A first bearing 20 is configured for the relative axial positioning of the rotor 70 and the housing 80 with respect to one another and for receiving an axial force resulting from the arrangement of the first permanent magnet 30 and the second permanent magnet 40, and a second bearing 10 and a third bearing 90 are configured for receiving radial forces and for positioning the axis of rotation of the second permanent magnet 40.

The invention claimed is:

1. A heart support system, comprising:
   a rotor bearing system comprising:
      a housing, wherein a first permanent magnet is mounted within the housing and configured to rotate about a first axis;
      a rotor configured to convey a liquid, wherein the rotor comprises a second permanent magnet, wherein the second permanent magnet comprises a hollow-cylindrical permanent magnet and is configured to rotate about a second axis;
      wherein the first permanent magnet and the second permanent magnet at least partially overlap axially,
      wherein the first permanent magnet is axially offset relative to the second permanent magnet,
      wherein the first permanent magnet and the second permanent magnet are arranged to produce an axial force;
      wherein the housing is positioned between the first permanent magnet and the second permanent magnet in an axial overlap region of the first permanent magnet and the second permanent magnet;
      a first bearing configured to provide a relative axial positioning of the rotor and the housing with respect to one another and configured to receive the axial force resulting from the arrangement of the first permanent magnet and the second permanent magnet; and
      a second bearing, wherein the first bearing and the second bearing are configured to receive radial forces and configured to position the second axis of the second permanent magnet.

2. The heart support system according to claim 1, wherein the first bearing is disposed between the housing and the rotor and the second bearing is disposed on the rotor.

3. The heart support system according to claim 1, wherein the first bearing is disposed on the rotor and the second bearing is disposed between the housing and the rotor.

4. The heart support system according to claim 1, wherein the housing is a motor housing comprising a rotatably mounted shaft within an interior of the motor housing, and wherein the first permanent magnet is disposed on the rotatably mounted shaft.

5. The heart support system according to claim 1, wherein the first permanent magnet and the second permanent magnet are arranged coaxially.

6. The heart support system according to claim 1, wherein each of the first permanent magnet and the second permanent magnet comprise at least one pair of poles, wherein the first permanent magnet and the second permanent magnet comprise an equal number of pairs of poles.

7. The heart support system according to claim 1, wherein the axial force resulting from the arrangement of the first permanent magnet and the second permanent magnet is configured to be greater than a hydraulic force acting on the rotor.

8. The heart support system according to claim 1, wherein each of the first permanent magnet and the second permanent magnet comprises at least two axial segments.

9. The heart support system according to claim 1, wherein the first permanent magnet and/or the second permanent magnet comprises a radial, parallel or diametrical magnetization.

10. The heart support system according to claim 1, wherein the first permanent magnet and/or the second permanent magnet comprises a Halbach array.

11. A heart support system, comprising:
a rotor bearing system comprising:
  a housing, wherein a first permanent magnet is mounted within the housing and configured to rotate about a first axis;
  a rotor configured to convey a liquid, wherein the rotor comprises a second permanent magnet, wherein the second permanent magnet is a hollow-cylindrical permanent magnet and is configured to rotate about a second axis;
  wherein the first permanent magnet and the second permanent magnet at least partially overlap axially,
  wherein the first permanent magnet is axially offset relative to the second permanent magnet,
  wherein the first permanent magnet and the second permanent magnet are arranged to produce an axial force;
  wherein the housing is positioned between the two permanent magnets in an axial overlap region of the first permanent magnet and the second permanent magnet;
  a first bearing configured to provide a relative axial positioning of the rotor and the housing with respect to one another and configured to receive the axial force resulting from the arrangement of the first permanent magnet and the second permanent magnet; and
  a second bearing and a third bearing, wherein the second bearing and the third bearing are configured to receive radial forces and configured to position the second axis of the second permanent magnet.

12. The heart support system according to claim 11, wherein the first bearing and the third bearing are disposed between the housing and the rotor and the second bearing is disposed on the rotor.

13. The heart support system according to claim 11, wherein the first bearing and the third bearing are disposed on the rotor and the second bearing is disposed between the housing and the rotor.

14. The heart support system according to claim 11, wherein the housing is a motor housing comprising a rotatably mounted shaft within an interior of the motor housing, and wherein the first permanent magnet is disposed on the rotatably mounted shaft.

15. The heart support system according to claim 11, wherein the first permanent magnet and the second permanent magnet are arranged coaxially.

16. The heart support system according to claim 11, wherein each of the first permanent magnet and the second permanent magnet comprise at least one pair of poles, wherein the first permanent magnet and the second permanent magnet comprise an equal number of pairs of poles.

17. The heart support system according to claim 11, wherein the axial force resulting from the arrangement of the first permanent magnet and the second permanent magnet is configured to be greater than a hydraulic force acting on the rotor.

18. The heart support system according to claim 11, wherein each of the first permanent magnet and the second permanent magnet comprises at least two axial segments.

19. The heart support system according to claim 11, wherein the first permanent magnet and/or the second permanent magnet comprises a radial, parallel or diametrical magnetization.

20. The heart support system according to claim 11, wherein the first permanent magnet and/or the second permanent magnet comprises a Halbach array.

* * * * *